(12) United States Patent
Morikawa

(10) Patent No.: US 7,503,356 B2
(45) Date of Patent: Mar. 17, 2009

(54) LIQUID SUPPLY APPARATUS

(75) Inventor: Hideyuki Morikawa, Tokyo (JP)

(73) Assignee: Uniflows Co., Ltd., Tokyo (JP)

( * ) Notice: Subject to any disclaimer, the term of this patent is extended or adjusted under 35 U.S.C. 154(b) by 249 days.

(21) Appl. No.: 11/432,933

(22) Filed: May 12, 2006

(65) Prior Publication Data

US 2006/0254509 A1   Nov. 16, 2006

(30) Foreign Application Priority Data

May 12, 2005   (JP)   ............................ 2005-139217
Jun. 28, 2005   (JP)   ............................ 2005-187514

(51) Int. Cl.
*B67C 3/26*   (2006.01)
(52) U.S. Cl. .................... 141/250; 141/130; 901/17; 901/25
(58) Field of Classification Search ............... 141/250, 141/86, 130, 137, 135, 129, 98, 100, 237; 422/67, 100; 222/63; 901/25, 17
See application file for complete search history.

(56) References Cited

U.S. PATENT DOCUMENTS

| | | | |
|---|---|---|---|
| 3,265,100 A * | 8/1966 | Holm et al. | 141/284 |
| 3,820,545 A * | 6/1974 | Jefferts | 606/117 |
| 4,166,483 A * | 9/1979 | Nordlund | 141/1 |
| 4,630,992 A * | 12/1986 | Gilli et al. | 414/744.6 |
| 4,757,437 A * | 7/1988 | Nishimura | 700/64 |
| 5,046,539 A * | 9/1991 | MacLeish et al. | 141/234 |
| 5,186,394 A * | 2/1993 | Tsuji | 239/587.4 |
| 5,431,201 A * | 7/1995 | Torchia et al. | 141/98 |
| 5,443,791 A * | 8/1995 | Cathcart et al. | 422/65 |
| 5,479,969 A * | 1/1996 | Hardie et al. | 141/130 |
| 5,610,069 A * | 3/1997 | Clark et al. | 436/49 |
| 5,647,410 A * | 7/1997 | Nakagawa et al. | 141/67 |
| 6,727,608 B2 * | 4/2004 | Yamawaki et al. | 310/49 R |

FOREIGN PATENT DOCUMENTS

JP   07-140127   6/1995

* cited by examiner

*Primary Examiner*—Timothy L Maust
*Assistant Examiner*—Jason K Niesz
(74) *Attorney, Agent, or Firm*—Myers Bigel Sibley & Sajovec, P.A.

(57) ABSTRACT

There is provided a low-cost liquid supply apparatus using a system in which a liquid nozzle is moved, the apparatus being configured so that the installation area of the apparatus is small, a liquid vessel can be installed or removed easily without being hindered by equipment for moving the liquid nozzle, and further the number of parts is small. The liquid nozzle is attached to an arm capable of being turned reversibly around a turning shaft, and the movement of the liquid nozzle is controlled by the turning angle of the arm for either one axis of the X-axis and the Y-axis and is controlled by changing the length of the arm from the turning shaft for the other axis.

1 Claim, 2 Drawing Sheets

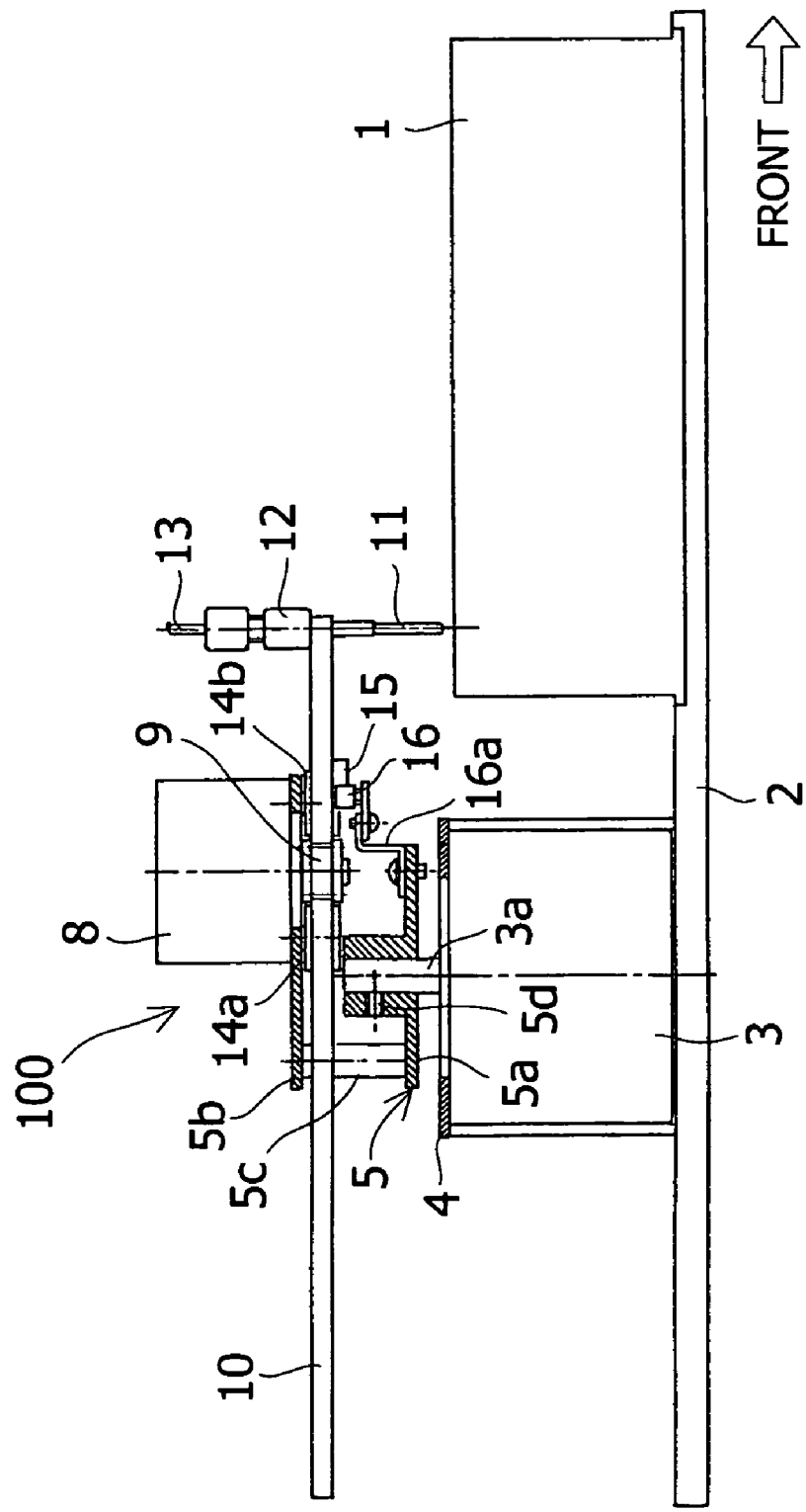

LIQUID SUPPLY APPARATUS

RELATED APPLICATIONS

This application claims priority from Japanese Patent Application No. 2005-139217; filed May 12, 2005, and Japanese Patent Application No. 2005-187514; filed Jun. 28, 2005, the disclosures of which are incorporated herein by reference in their entireties.

BACKGROUND AND FIELD OF THE INVENTION

The present invention relates to a liquid supply apparatus configured so that a liquid vessel is fixed on a base, and a liquid nozzle having a supply port for supplying a liquid into the liquid vessel can be moved to a necessary position of the liquid vessel on the X- and Y-axis coordinates.

As a fraction collector for collecting a liquid coming out of a preparative chromatograph column for separating and refining mixed substances or a liquid coming out of a reactor, the following two systems are generally used.

(1) A system in which a receptacle is moved, and a fraction nozzle having a supply port for supplying a liquid into the receptacle is fixed As this system, there are available a system in which the receptacle is moved in the directions of two axes of X and Y and a turntable system in which the receptacle is moved rotatingly. After every operation, the receptacle is removed after liquid collection and a new receptacle is installed.

(2) A system in which the receptacle is fixed, and the fraction nozzle is moved

As this system, a system in which the fraction nozzle is moved in the directions of two axes of X and Y as disclosed, for example, in Patent Document 1 (Japanese Patent Provisional Publication No. 7-140127) is used mainly.

In such a system, the fraction nozzle is guided by guide rails in the X-axis direction and the Y-axis direction, and is driven via a ball screw and a timing belt. Also, the fraction nozzle is arranged above the receptacle, and a driving system such as the ball screw and the timing belt is also arranged above or at the side of the receptacle.

In this system as well, after every operation, the receptacle is removed after liquid collection and a new receptacle is installed.

The system in which the receptacle is moved, and the fraction nozzle having the supply port for supplying a liquid into the receptacle is fixed as in the above-described item (1) has an advantage that the pipe for the fraction nozzle is short, but has a problem in that the installation area of the apparatus is large.

On the other hand, the system in which the receptacle is fixed and the fraction nozzle is moved as in the above-described item (2) has an advantage that the installation area of the apparatus is smaller than that in the system of the item (1), but has a problem in that the pipe for the fraction nozzle is long because the fraction nozzle is moved.

In installing the fraction collector at a limited place in a draft chamber or a cleaning box, the system of the item (2) in which the installation area of the apparatus is small, namely, the system in which the receptacle is fixed and the fraction nozzle is moved must be used inevitably.

However, in the case where the system in which the receptacle is fixed and the fraction nozzle is moved as in the item (2) is used, there arises a problem in that the pipe for the fraction nozzle is long because the fraction nozzle is moved as described above. Also, if the apparatus is designed so as to have a small size, when the receptacle is installed or removed, a driving unit for moving the fraction nozzle and the guide rails in the X-axis direction and the Y-axis direction become a hindrance to the installation or removal work, so that it is difficult to install or remove the receptacle. On the other hand, if the occurrence of this problem is avoided, the size of the apparatus increases.

Also, in the system of the item (2), since the configuration is such that the fraction nozzle is moved, the number of parts increases, resulting in a high cost.

SUMMARY OF THE INVENTION

The present invention has been made in view of the above circumstance, and accordingly an object thereof is to provide a low-cost liquid supply apparatus using a system in which a liquid nozzle is moved, the apparatus being configured so that the installation area of the apparatus is small, a liquid vessel can be installed or removed easily without being hindered by equipment for moving the liquid nozzle, and further the number of parts is small.

In accordance with the first embodiment of the present invention, there is provided a liquid supply apparatus, comprising: a liquid vessel fixed on a base; and a liquid nozzle for supplying a liquid into the liquid vessel, being movable on X- and Y-axis coordinates to a necessary position of the liquid vessel; the liquid nozzle being attached to an arm capable of being turned reversibly around a turning shaft, by which movement of the liquid nozzle is controlled by a turning angle of the arm for either one axis of the X-axis and the Y-axis and the liquid nozzle being controlled by changing a length of the arm from the turning shaft for the other axis.

In the first embodiment, it is preferable that a movement control means for a fraction nozzle be specifically configured so as to be as described in following embodiment 1-ii or 1-iii.

In embodiment 1-ii, the liquid supply apparatus further comprises a rack provided on the arm fitted with the liquid nozzle, the arm being guided by a guide member; and a pinion gear that engages with the rack and is rotatably driven by a driving unit; wherein the pinion gear is rotatably driven by the driving unit to reciprocate the rack, and the arm is moved by being guided by the guide member, by which the length from the rotating shaft is changed.

Also, in embodiment 1-iii, the arm fitted with the liquid nozzle is guided by a guide member; and further comprises a friction drive roller which is rotatably driven by the driving unit; by which the friction drive roller and the arm are brought into friction contact with each other by pushing the friction drive roller on the arm while the friction drive roller is rotatably driven by the driving unit, and the length from the rotating shaft is changed by moving the arm by being guided by the guide member.

In accordance with the second embodiment of the present invention, there is provided a liquid supply apparatus, comprising: a liquid vessel being fixed on a base, and a liquid nozzle for supplying a liquid into the liquid vessel, being movable on X- and Y-axis coordinates to a necessary position of the liquid vessel, the liquid nozzle being attached to an arm that enables the liquid nozzle to move to above the liquid vessel; a support block that can turn the arm reversibly around a turning shaft and reciprocatingly supports the arm; an arm turning unit for reversibly turning the arm via the support block; and an arm reciprocating unit for reciprocating the arm in a state of being supported on the support block; wherein the movement of the liquid nozzle is controlled by a turning angle of the arm by using the arm turning unit for either one axis of the X-axis and the Y-axis and the movement of the liquid nozzle is controlled by changing the length of the arm from the turning shaft by using the arm reciprocating unit for the other axis.

In the second embodiment, it is preferable that the liquid supply apparatus be specifically configured so as to be as described in following embodiment 2-ii or 2-iii.

In embodiment 2-ii, the arm turning unit is formed by a stepping motor; the support block is fixed on an output shaft of the stepping motor so as to be capable of turning reversibly together with the output shaft; and the arm is supported on the support block so as to be capable of being reciprocated by the arm reciprocating unit, and by reversibly turning the arm via the support block by the stepping motor, control of the turning angle of the arm is carried out for either one axis of the X-axis and the Y-axis, and by reciprocating the arm by the arm reciprocating unit in a state of being supported on the support block, control for changing the length of the arm from the turning shaft is carried out for the other axis.

In embodiment 2-iii, the liquid vessel is fixed on one end side on the base and the stepping motor is installed on the other end side thereon with the output shaft being vertical, the support block is fixed in an upper end portion of the output shaft, and the arm is supported reciprocatingly on the support block in a state so as to be substantially at right angles to the output shaft and supported on the support block so that the liquid nozzle comes to an arbitrary position above the receptacle.

According to the present invention, in the liquid supply apparatus, as in the first embodiment, the liquid nozzle having the supply port for supplying a liquid into the liquid vessel is attached to the arm capable of turning reversibly around the turning shaft, and the movement of the liquid nozzle is controlled by the turning angle of the arm for either one axis of the X-axis and the Y-axis and is controlled by changing the length of the arm from the turning shaft for the other axis.

Specifically, as in the second embodiment, the support block is fixed on the turning shaft consisting of the output shaft of the stepping motor forming the arm turning unit, the arm is supported on the support block together with the turning shaft so as to be capable of turning reversibly and the arm is supported on the support block so as to be capable of being reciprocated by the arm reciprocating unit, and by reversibly turning the arm via the support block by the stepping motor, control of the turning angle of the arm is carried out for either one axis of the X-axis and the Y-axis, and by reciprocating the arm by the arm reciprocating unit in a state of being supported on the support block, control for changing the length of the arm from the turning shaft is carried out for the other axis.

Accordingly, by reversibly turning the support block by the stepping motor forming the arm turning unit, the liquid nozzle attached to the end portion of the arm is moved in the axis direction of either one of the X-axis and the Y-axis (for example, the X-axis direction), and also by reciprocatingly supporting the arm on the support block, the arm and the liquid nozzle are reciprocated in the other axis direction (for example, the Y-axis direction) by the arm reciprocating unit. Thereby, the liquid nozzle can be moved freely above the liquid vessel so as to be capable of supplying a liquid to a necessary position of the liquid vessel.

Accordingly, by reversibly turning the support block and by freely moving the arm and the liquid nozzle, which are reciprocatingly supported on the support block, above the liquid vessel, the liquid vessel can be installed or removed easily without being hindered by a liquid nozzle driving system such as the support block and the arm.

Also, by the configuration such that the support block fixed on the output shaft of the stepping motor forming the arm turning unit is turned reversibly, and the arm, which is supported reciprocatingly on the support block, and the liquid nozzle are reciprocated by the arm reciprocating unit, the liquid nozzle can be moved freely in both directions of X-axis and Y-axis. Accordingly, the construction is small and compact, and the installation area of the apparatus is small. Further, driving mechanisms such as a guide rail, ball screw, and timing belt that are needed in the conventional art are unnecessary, so that a low-cost apparatus in which the construction is simple and the number of parts is small can be obtained.

BRIEF EXPLANATION OF THE DRAWINGS

FIG. 3 is a side view of the liquid supply apparatus shown in FIG. 1 (a view taken in the direction of the arrow B of FIG. 2).

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

Figure 1:
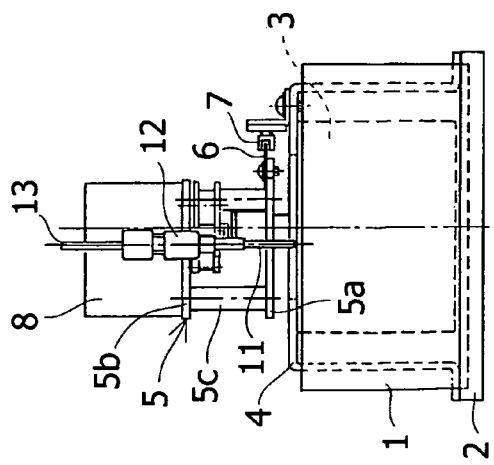
FIG. 1 is a front view of a liquid supply apparatus consisting of a fraction collector in accordance with an embodiment of the present invention (a view taken in the direction of the arrow A of FIG. 2).
Figure 2:
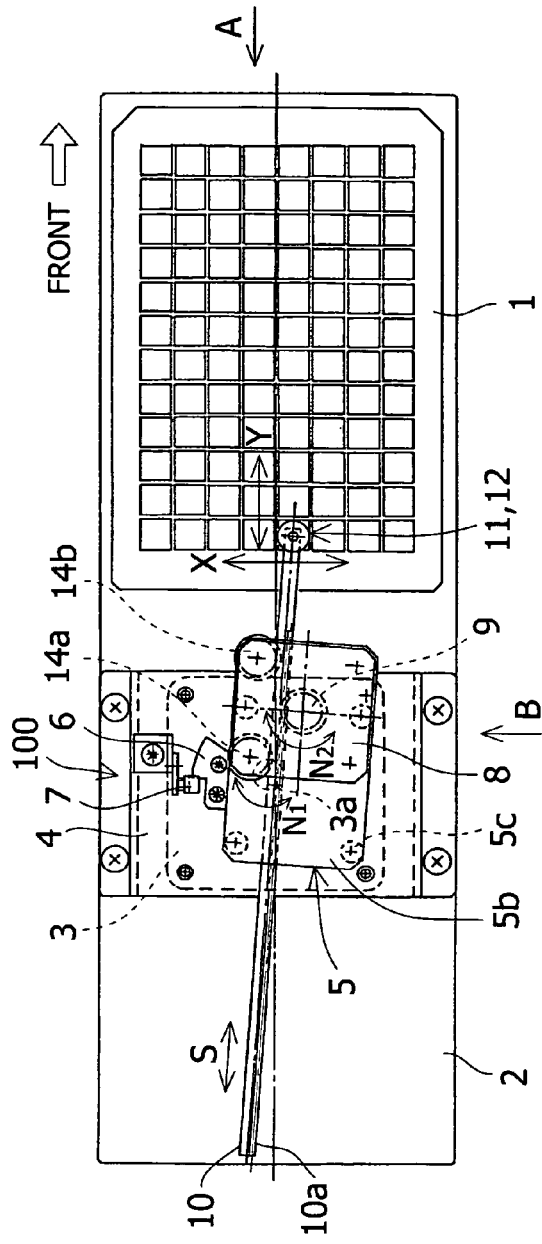
FIG. 2 is a plan view of the liquid supply apparatus shown in FIG. 1.

FIG. 1 is a front view of a liquid supply apparatus consisting of a fraction collector in accordance with an embodiment of the present invention (a view taken in the direction of the arrow A of FIG. 2), FIG. 2 is a plan view of the liquid supply apparatus shown in FIG. 1, and FIG. 3 is a side view of the liquid supply apparatus shown in FIG. 1 (a view taken in the direction of the arrow B of FIG. 2).

FIGS. 1 to 3 shows a receptacle 1 fixed in a concave portion formed on the front side a base 2. In this example, the receptacle 1 is formed by using a 96-hole deep well; however, it can be formed by arranging a plurality of test tubes in the X and Y directions.

A fraction nozzle driving mechanism 100 is installed on the rear side on the base 2. The fraction nozzle driving mechanism 100 is configured as described below.

An X-axis drive motor 3 is provided which consists of a stepping motor, and is fixed on the base 2 via a motor fitting member 4 with an output shaft 3a being vertical.

A Y-axis drive block 5 (support block) is formed by connecting a plate-shaped lower member 5a to a plate-shaped upper member 5b by a plurality of (four in this example)

connecting stays 5*c*. The lower member 5*a* of the Y-axis drive block 5 is fixed to the upper end portion of the output shaft 3*a* of the X-axis drive motor 3 via a fixing screw 5*d,* and thereby the Y-axis drive block 5 can be turned reversibly together with the output shaft 3*a*.

An X-axis shutter 6 is installed at the side of the Y-axis drive block 5, and an X-axis origin sensor 7 is installed on the base 2. The positioning of a fraction nozzle 11, described later, in the X-axis direction (essentially right and left direction) is performed by the X-axis shutter 6 and the X-axis origin sensor 7.

On the Y-axis drive block 5, a Y-axis drive motor 8 is installed with an output shaft (not shown) thereof being vertical and directed downward. A pinion gear 9 is fixed on the output shaft of the Y-axis drive motor 8.

An arm 10 is formed into a rod shape extending in the front and rear direction. The arm 10 is supported on the Y-axis drive block 5 so as to be capable of reciprocating freely in the front and rear direction (Y-axis direction), and reciprocates on the Y-axis drive block 5 by being guided by a plurality of (two in this example) guide rollers 14*a* and 14*b*.

On the front tip end of the arm 10, the fraction nozzle 11 having a supply port for supplying a liquid is installed via a nozzle holder 12. A pipe 13 is connected to the fraction nozzle 11. The liquid is supplied from a liquid outlet of a preparative column etc., not shown, to the fraction nozzle 11 via the pipe 13.

The arm 10 is provided engravingly with a rack 10*a* along the lengthwise direction so that the rack 10*a* engages with the pinion gear 9. A plurality of (two in this example) guide rollers 14*a* and 14*b* are disposed in the lengthwise direction.

Accordingly, the pinion gear 9 is rotatingly driven by the Y-axis drive motor 8 to reciprocate the rack 10*a*, and thereby the arm 10 is reciprocated in the front and rear direction of the receptacle 1 as indicated by the arrow S in FIG. 2 by being guided by the guide rollers 14*a* and 14*b*. Thereby, the length of the arm 10 from the rotation axis of the output shaft 3*a* of the X-axis drive motor 3 can be changed.

The arm 10 can be supported reciprocatingly by a slide bearing in place of the guide rollers 14*a* and 14*b*.

In place of the combination of the rack 10*a* and the pinion gear 9, a friction drive roller can be used.

That is to say, as the drawings may alternatively depict, the arm 10 fitted with the fraction nozzle 11 is guided by the guide rollers 14*a* and 14*b,* and a friction drive roller 9 rotatingly driven by the Y-axis drive motor 8 is provided. The friction drive roller 9 and the arm 10 are brought into friction contact with each other by pushing the friction drive roller on the arm surface 10*a* while the friction drive roller is rotatingly driven by the Y-axis drive motor 8, by which the arm 10 is moved by being guided by the guide rollers 14*a* and 14*b*. Thereby, the length of the arm 10 from the rotation axis of the output shaft 3*a* of the X-axis drive motor 3 can be changed.

In this case, the machining of tooth profile, which is necessary for the rack 10*a* and the pinion gear, is not needed, which results in a low cost.

In FIG. 3, a Y-axis shutter 15 is attached to the arm 10, and a Y-axis origin sensor 16 is attached to the Y-axis drive block 5 via a bracket 16*a*. The positioning in the Y-axis direction (essentially the front and rear direction) of the fraction nozzle 11, described above, is performed by the Y-axis shutter 15 and the Y-axis origin sensor 16.

For the X-axis drive motor 3 consisting of a stepping motor and the Y-axis drive motor 8 consisting of a stepping motor, the reversible turning or reversible rotation thereof is controlled by a motor controller, not shown.

By the above-described configuration, the fraction nozzle 11 installed in the tip end portion of the arm 10 is reversibly turned in the direction of N1 together with the arm 10 by the X-axis drive motor 3 consisting of a stepping motor as shown in FIG. 2, by which the fraction nozzle 11 is reciprocated in the X-axis direction (essentially the right and left direction). Also, the pinion gear 9 is reversibly driven rotatingly in the direction of N2 by the Y-axis drive motor 8 and thereby the rack 10*a* is reciprocated, by which the fraction nozzle 11 is reciprocated in the Y-axis direction (essentially the front and rear direction). Thus, the fraction nozzle 11 moves freely in the directions of two axes of X and Y, so that a liquid can be poured into a desired hole in the receptacle 1.

Next, the operation of this embodiment is explained.

The power supply, not shown, for the apparatus is turned on. When the X-axis origin sensor 7 does not detect the X-axis shutter 6, the X-axis drive motor 3 consisting of a stepping motor is turned in the left direction, and when the X-axis origin sensor 7 detects the X-axis shutter 6, the X-axis drive motor 3 is turned in the right direction. Then, when the X-axis origin sensor 7 does not detect the X-axis shutter 6, the X-axis drive motor 3 is turned in the left direction, and the position at which the X-axis shutter 6 changes from the non-detected state to the detected state is made the origin of the X-axis drive motor 3.

Next, when the Y-axis origin sensor 16 does not detect the Y-axis shutter 15, the Y-axis drive motor 8 consisting of a stepping motor is turned, for example, in the left direction to move the arm 10 and the fraction nozzle 11 to the rear of the receptacle 1, and when the Y-axis origin sensor 16 detects the Y-axis shutter 15, the arm 10 and the fraction nozzle 11 are moved to the front of the receptacle 1. Then, when the Y-axis origin sensor 16 does not detect the Y-axis shutter 15, the Y-axis drive motor 8 is turned, for example, in the left direction to move the arm 10 and the fraction nozzle 11 to the rear, and the position at which the Y-axis shutter 15 changes from the non-detected state to the detected state is made the origin of the Y-axis drive motor 8.

After the origins of the X-axis drive motor 3 and the Y-axis drive motor 8 have been detected in the above-described manner, the arm 10 and the fraction nozzle 11 are moved to a position at which the arm 10 and the fraction nozzle 11 do not become a hindrance to the installation and removal of the receptacle 1, and the soft origin is set.

After the soft origin of the arm 10 and the fraction nozzle 11 has been set, the reversible turning of the X-axis drive motor 3 consisting of a stepping motor in the direction of N1 in FIG. 2 is controlled by the motor controller, not shown, by which the arm 10 and the fraction nozzle 11 are reciprocated in the X-axis direction (essentially the right and left direction). By controlling the reversible rotation in the direction of N2 in FIG. 2 of the Y-axis drive motor 8 and the pinion gear 9, the arm 10 and the fraction nozzle 11 are reciprocated in the Y-axis direction (essentially the front and rear direction) via the rack 10*a*.

Thus, the position of the fraction nozzle 11 is set above the hole of the receptacle 1, and the pouring of a liquid from the fraction nozzle 11 into the hole is finished. Thereafter, the fraction nozzle 11 is returned to the soft origin, by which the pouring operation is finished.

By the above-described operation, the arm 10 and the fraction nozzle 11 are moved freely in the directions of two axes of X and Y above the receptacle 1, and thereby a liquid can be poured into a desired hole of the receptacle 1.

As described above, according to this embodiment, the fraction nozzle 11 having the supply port for supplying a liquid into the receptacle 1 is configured so that the Y-axis drive block (support block) 5 is fixed on the output shaft 3*a* of the X-axis drive motor 3 consisting of a stepping motor; the arm 10 is supported on the Y-axis drive block 5 together with the output shaft 3*a* so as to be turnable reversibly; and the arm 10 is supported on the Y-axis drive block 5 in such a manner as to be capable of being reciprocated by the Y-axis drive motor 8 consisting of a stepping motor, by which control of the turning angle of the arm 10 with respect to the X axis is carried out by reversibly turning the arm 10 via the Y-axis drive block 5 by the X-axis drive motor 3, and control such that the length of the arm 10 from the output shaft 3*a* is changed with respect to the Y-axis direction is carried out by reciprocating the arm 10 by the Y-axis drive motor 8 in a state of being supported on the Y-axis drive block 5.

Accordingly, by reversibly turning the Y-axis drive block 5 by the X-axis drive motor 3 consisting of a stepping motor, the fraction nozzle 11 attached to the end portion of the arm 10 can be moved in the X-axis direction, and by reciprocatingly supporting the arm 10 on the Y-axis drive block 5 and by moving the arm 10 and the fraction nozzle 11 in the Y-axis direction by Y-axis drive motor 8 consisting of a stepping motor, the fraction nozzle 11 can be moved freely above the receptacle 1 so as to be capable of supplying a liquid to a necessary position of the receptacle 1.

Accordingly, by reversibly turning the Y-axis drive block 5 and by freely moving the arm 10, which is supported reciprocatingly on the Y-axis drive block 5, and the fraction nozzle 11 above the receptacle 1, the receptacle 1 can be installed or removed easily without being hindered by a fraction nozzle driving system such as the Y-axis drive block 5 and the arm 10.

Also, by the configuration such that the Y-axis drive block 5 fixed on the output shaft 3*a* of the X-axis drive motor 3 consisting of a stepping motor is turned reversibly, and the arm 10 supported reciprocatingly on the Y-axis drive block 5 and the fraction nozzle 11 are reciprocated, the fraction nozzle 11 can be moved freely in both of the X-axis and the Y-axis. Accordingly, the construction is small and compact, and the installation area of the apparatus is small. Further, driving mechanisms such as a guide rail, ball screw, and timing belt that are needed in the conventional art are unnecessary, so that a low-cost apparatus in which the construction is simple and the number of parts is small can be obtained.

According to the present invention, there can be provided a low-cost liquid supply apparatus using a system in which a liquid nozzle is moved, the apparatus being configured so that the installation area of the apparatus is small, a liquid vessel can be installed or removed easily without being hindered by equipment for moving the liquid nozzle, and further the number of parts is small.

While the present invention has been described in terms of the preferred embodiments, those skilled in the art will recognize that the present invention can be practiced with modification within the spirit and scope of the appended claims.

What is claimed is:

1. A liquid supply apparatus, comprising:
    a liquid vessel fixed on a base; and
    a liquid nozzle for supplying a liquid into the liquid vessel, being movable on X- and Y-axis coordinates to a necessary position of the liquid vessel,
    wherein: the liquid nozzle is attached to an arm capable of being turned reversibly around a turning shaft by which movement of the liquid nozzle is controlled by a turning angle of the arm for either one axis of the X-axis and the Y-axis; the liquid nozzle is controlled by changing a length of the arm from the turning shaft for the other axis; and the arm fitted with the liquid nozzle is guided by a guide member, wherein said liquid supply apparatus further comprises a friction drive roller which is rotatably driven by the driving unit,
    by which the friction drive roller and the arm are brought into friction contact with each other by pushing the friction drive roller on the arm while the friction drive roller is rotatably driven by the driving unit, and the length from the rotating shaft is changed by moving the arm by being guided by the guide member.

* * * * *